(12) United States Patent
Ooshika et al.

(10) Patent No.: US 9,622,960 B2
(45) Date of Patent: Apr. 18, 2017

(54) HAIR COSMETIC COMPOSITION

(71) Applicant: KAO CORPORATION, Chuo-ku (JP)

(72) Inventors: Masato Ooshika, Chiba (JP); Chie Sakaguchi, Chiyoda-ku (JP); Koji Yui, Utsunomiya (JP)

(73) Assignee: KAO CORPORATION, Chuo-ku (JP)

( * ) Notice: Subject to any disclaimer, the term of this patent is extended or adjusted under 35 U.S.C. 154(b) by 0 days.

(21) Appl. No.: 14/387,733

(22) PCT Filed: May 14, 2013

(86) PCT No.: PCT/JP2013/063881
§ 371 (c)(1),
(2) Date: Sep. 24, 2014

(87) PCT Pub. No.: WO2013/172475
PCT Pub. Date: Nov. 21, 2013

(65) Prior Publication Data
US 2015/0150778 A1 Jun. 4, 2015

(30) Foreign Application Priority Data

May 15, 2012 (JP) ................... 2012-111357

(51) Int. Cl.
*A61K 8/86* (2006.01)
*A61Q 5/06* (2006.01)
*A61K 8/81* (2006.01)

(52) U.S. Cl.
CPC .............. *A61K 8/86* (2013.01); *A61K 8/8152* (2013.01); *A61Q 5/06* (2013.01); *A61K 2800/594* (2013.01)

(58) Field of Classification Search
CPC .. A61K 2800/594; A61K 8/8152; A61K 8/86; A61Q 5/06
See application file for complete search history.

(56) References Cited

U.S. PATENT DOCUMENTS

| | | | |
|---|---|---|---|
| 6,074,628 A | 6/2000 | Bolich et al. | |
| 6,113,883 A | 9/2000 | Midha et al. | |
| 6,395,262 B1 | 5/2002 | Favre et al. | |
| 6,946,436 B2 * | 9/2005 | Wakamatsu | A61K 8/062 424/400 |
| 2011/0008266 A1 | 1/2011 | Tamarkin et al. | |
| 2012/0027710 A1 | 2/2012 | Shimizu et al. | |
| 2012/0039834 A1 | 2/2012 | Oshika et al. | |
| 2012/0045410 A1 | 2/2012 | Toyoda et al. | |
| 2012/0164092 A1 | 6/2012 | Kurashima et al. | |
| 2012/0201775 A1 | 8/2012 | Toyoda et al. | |
| 2012/0230934 A1 | 9/2012 | Doi et al. | |
| 2012/0251472 A1 | 10/2012 | Kurashima et al. | |

FOREIGN PATENT DOCUMENTS

| | | |
|---|---|---|
| CN | 101674864 A | 3/2010 |
| CN | 102046146 A | 5/2011 |
| DE | 10 2007 008089 | 8/2008 |
| EP | 2 191 813 A1 | 6/2010 |
| EP | 2 420 220 | 2/2012 |
| EP | 2 420 220 A1 | 2/2012 |
| EP | 2 425 811 | 3/2012 |
| JP | 2001 507368 | 6/2001 |
| JP | 2004 143074 | 5/2004 |
| JP | 2007-106678 | 4/2007 |
| JP | 2010 126523 | 6/2010 |
| JP | 2010 168294 | 8/2010 |
| JP | 2010 235499 | 10/2010 |
| JP | 2010 275291 | 12/2010 |
| JP | 2011 068646 | 4/2011 |
| TW | 201105359 A1 | 2/2011 |
| WO | 2009 090558 | 7/2009 |
| WO | WO 2011/059063 | 5/2011 |

OTHER PUBLICATIONS

Ravindran et al. (Malaysian Journal of Pharmaceutical Sciences (2012;10(1):61-73).*
Declaration by Applicant filed Sep. 15, 2016; 9 pages.*
"Neutralizing Carbopol® and Pemulen(8) Polymers in Aqueous and Hydroalcoholic Systems", NOVEON, Total 3 Pages, (Jan. 2002) XP05004496.
"Personal Care Technical Information Pluracare L/F Grades Poloxamer = Registered Trademark of BASF Group", Total 10 Pages, (Jul. 1, 2009) XP055118205.
International Search Report and Written Opinion Issued May 27, 2014 in PCT/JP13/063881 Filed May 14, 2013.
"Neutralizing Carbopols and Pemulens Polymers in Aqueous and Hydroalcoholic Systems", *Lubrizol*, Sep. 16, 2009, pp. 1-3.

* cited by examiner

*Primary Examiner* — Ernst V Arnold
(74) *Attorney, Agent, or Firm* — Oblon, McClelland, Maier & Neustadt, L.L.P.

(57) ABSTRACT

A hair cosmetic composition comprising the following components (A) and (B) and having a pH of 6 or less: (A) an oxyalkylene polymer represented by the following general formula (a1): -(AO)$_n$— (a1) wherein A represents an alkylene group having 2 to 6 carbon atoms and n represents a number from 50 to 30,000, provided that n number of AOs consist of at least two alkyleneoxy groups and are arranged through either random polymerization or block polymerization; and (B) a polymer containing a component unit represented by the following general formula (b1) and a component unit represented by the following general formula (b2) in a mass ratio (b1)/(b2) of 50/50 to 100/0: —(CH$_2$CR$^1$COOH)— (b1) —(CH$_2$CR$^2$COOR$^3$)— (b2) wherein R$^1$ and R$^2$ represent H or CH$_3$ and R$^3$ represents a C$_{2-20}$ hydrocarbon group.

21 Claims, No Drawings

HAIR COSMETIC COMPOSITION

FIELD OF THE INVENTION

The present invention relates to a hair cosmetic composition comprising a specific polymer.

BACKGROUND OF THE INVENTION

In order to improve the set retention of a hair cosmetic composition, the content of a set polymer or an oil component is generally increased. If the content of a set polymer is simply increased, however, the setting the hairstyle with the hair cosmetic composition may become hard and stiff. Besides, when a hair cosmetic composition containing a set polymer is used, if the hairstyle set with the hair cosmetic composition once becomes disheveled, the hair generally cannot be restyled. On the other hand, when a hair cosmetic composition containing an oil component is used, the hair can be restyled after the hairstyle is disheveled; however the set retention is much weaker than that obtained by using a set polymer. If the content of the oil component is increased for improving the set retention, the hair set with such a hair cosmetic composition becomes sticky.

Therefore, a hair cosmetic composition using a specific set polymer for enabling hair restyling has been proposed (for example, Patent Document 1). Using such a set polymer enabling hair restyling causes, however, stickiness if sufficient set retention is provided, and on the other hand, if a less sticky polymer is used, sufficient set retention cannot be obtained. Thus, it is difficult to simultaneously obtain both performances.

An oxyalkylene polymer (polyalkylene glycol) has been used in a hair cosmetic composition for, for example, improving solubility, adjusting viscosity of a formulation, controlling feel, and providing plasticity. A hair cosmetic composition using such an oxyalkylene polymer, for example, using solid polyalkylene glycol and liquid polyalkylene glycol, and further using a film-forming polymer, for providing restyling performance and improving hair setting performance, is known (Patent Document 2).

Furthermore, an oxyalkylene polymer has also been used as a plasticizer for improving brittleness of a film-forming polymer used in a hair cosmetic composition. For example, a technique to obtain a hair cosmetic composition excellent in both hair setting performance and restyling performance by adding, to a specific hair set polymer, polyalkylene glycol in a substantially equivalent amount for providing adhesiveness is known (see Patent Document 3). Among these film-forming polymers, acidic polymers having, for example, a carboxy group in their structures are mostly available as neutralized products. Even when raw material is prepared or purchased as an acidic (not neutralized) type material, it is generally neutralized upon addition to a composition at about a neutral condition for securing its solubility and for easy cleaning properties of the dried film, and such an acidic type raw material is not used under acidic conditions.

On the other hand, in order to reduce the stickiness of a hair cosmetic composition containing a set polymer, the hair cosmetic composition has been conventionally improved by adding an oil component or a nonvolatile solvent for improving lubrication properties. When such a component is added, however, the ability to set the hair or the ability to restyling the hair may be hindered. As a countermeasure, there is a technique for withdrawing the stickiness of a hair cosmetic composition as well as to improve the hair set performance and the restyling performance, which have not been simultaneously obtained in the conventional techniques (see Patent Document 4). According to this technique, a polymer has adhesive properties characterized in that adhesion of the polymers itself (hereinafter referred to as the "self-adhesive force") is strong; on the other hand, adhesion to the other materials (hereinafter referred to as the "other-adhesive force") is weak (wherein the polymer having both properties of self-adhesive force and other-adhesive force will be hereinafter referred to as the "self-selective adhesiveness"). Such polymer having such self-selective adhesiveness is contained in the hair cosmetic composition of Patent Document 4, in order to obtain sufficient hair setting ability and ability to restyling the hair, and to reduce stickiness and stiffness of the hair. However, since the structure of a composition described in Patent Document 4 includes a carbonate bond, solvolysis is caused by water or ethanol, and therefore, long-term storage stability cannot be secured in a formulation system containing such a composition.

CITATION LIST

Patent Documents

[Patent Document 1] JP-A-2001-507368
[Patent Document 2] JP-A-2010-275291
[Patent Document 3] JP-A-2010-126523
[Patent Document 4] JP-A-2010-168294

SUMMARY OF THE INVENTION

The present invention provides a hair cosmetic composition comprising the following components (A) and (B) and having a pH of 6 or less:

(A) an oxyalkylene polymer represented by the following general formula (a1):

$$-(AO)_n-  \qquad (a1)$$

wherein A represents an alkylene group having 2 to 6 carbon atoms and n represents a number from 50 to 30,000, provided that n number of AOs consist of at least two alkyleneoxy groups and are arranged through either random polymerization or block polymerization; and (B) a polymer comprising a component unit (b1) represented by the following general formula (b1) and a component unit (b2) represented by the following general formula (b2) in a mass ratio (b1)/(b2) of 50/50 to 100/0:

$$-(CH_2CR^1COOH)-  \qquad (b1)$$

$$-(CH_2CR^2COOR^3)-  \qquad (b2)$$

wherein $R^1$ and $R^2$ represent a hydrogen atom or a methyl group and $R^3$ represents a hydrocarbon group having 2 to 20 carbon atoms.

The present invention further provides a method for hair styling comprising applying the above-described hair cosmetic composition to hair and setting a hairstyle.

The present invention further provides a use of the above-described hair cosmetic composition as a hair styling preparation.

DETAILED DESCRIPTION OF THE INVENTION

Conventionally, compositions having adhesiveness ability in hair preparations, including those of the aforementioned conventional techniques, in the case of using a substance which is solid at room temperature (such as a solid fat, a high molecular oxyalkylene polymer or a film-forming polymer), it has been necessary to use a liquid component for improving the adhesiveness, for obtaining compatibility or plasticization with a solvent or a low molecular compound of the same type, or for providing moisture or smoothness. As long as this method is employed, however, the stickiness to the hands and hair becomes more serious because of the increase of adhesiveness for improving the ability to set the hair and a sticky feeling on the fingers caused by the liquid component. Hence, the hair setting performance cannot be drastically improved at a high level nor the set hairstyle can be kept over a long period of time. Besides, even when these problems are solved by employing another means, the quality of the composition cannot be stabilized when stored for a long period of time.

Accordingly, the present invention relates to a hair cosmetic composition having sufficient hair setting performance and restyling performance, free from stickiness and stiffness, and enabling prevention of solvolysis under long term storage.

The present inventors have newly found the following: As polymers used in a hair cosmetic composition, an oxyalkylene polymer having a specific structure is combined with an acidic polymer having a specific structure in an acidic form, so as to be compatible with each other, and thus, adhesiveness at room temperature is provided. In addition, adhesiveness of the self-selective adhesiveness can be thus obtained as the characteristic of the polymers, and besides, long term storage stability can be secured. A hair cosmetic composition comprising such a combination of polymers has sufficient hair setting performance and restyling performance and is free from stickiness and stiffness.

<Method for Measuring Weight Average Molecular Weight>

In the present invention, the weight average molecular weight of the component (A), the component (B) and other polymers are defined as a value measured by gel permeation chromatography (GPC). More specifically, a weight average molecular weight is obtained from measurement value in terms of polystyrene by using a chromatograph of a trade name "HLC-8220GPC" (manufactured by Tosoh Corporation) as a GPC apparatus under the following GPC measurement conditions:

Measurement conditions for a polymer other than the component (B):
  Sample concentration: 0.25% by mass
  Sample amount: 100 µL
  Eluent: chloroform
  Flow rate: 1.0 mL/min
  Measurement temperature: 40° C.
  Column: trade name "K-G" (one column)+trade name "K-804L" (two columns) (both manufactured by Showa Denko)

Measurement conditions for a polymer as the component (B):
  Sample concentration: 0.25% by mass
  Sample amount: 100 µL
  Eluent: N,N-dimethylformamide solution (60 mmol/L $H_3PO_4$, 50 mmol/L LiBr)
  Flow rate: 1.0 mL/min
  Measurement temperature: 40° C.
  Column: trade name "TSKgel α-M" (two columns) (manufactured by Tosoh Corporation)

Furthermore, a detector and a standard sample are as follows:

Detector: differential refractometer (attached to the GPC apparatus, trade name "HLC-8220GPC" (manufactured by Tosoh Corporation))
  Polystyrene standard sample: "TSK standard POLYSTYRENE F-10" (molecular weight: 102,000), "F-1" (molecular weight: 10,200), "A-1000" (molecular weight: 870) (all manufactured by Tosoh Corporation), and "POLYSTYRENE STANDARD" (molecular weight: 900,000 or 30,000; manufactured by Nishio Kogyo KK)

[(A): Oxyalkylene Polymer]

In the general formula (a1), from the viewpoint of obtaining sufficient self-selective adhesiveness after drying the hair cosmetic composition, n is preferably 50 or more, more preferably 100 or more, and even more preferably 150 or more. Furthermore, from the viewpoint of showing sufficient self-selective adhesiveness after the hair cosmetic composition has dried after application on the hair and for not increasing the viscosity of the composition for ease of use, n is preferably 30,000 or less, more preferably 12,000 or less and even more preferably 4,000 or less.

Also in the general formula (1), A represents an alkylene group having 2 to 6 carbon atoms, and n number of AOs consists of a combination of at least two alkyleneoxy groups. The n number of AO is preferably a combination of two or more alkyleneoxy groups each having 2 to 4 carbon atoms, and more preferably a combination of alkyleneoxy groups respectively having 2 carbon atoms and 3 carbon atoms, namely, a combination of an ethyleneoxy group and a propyleneoxy group. Furthermore, the arrangement form of two or more AOs in $(AO)_n$ may be either random polymerization or block polymerization, and from the viewpoint of effectively showing an effect of combination with the component (B), the random polymerization is more preferably employed.

In the oxyalkylene polymer of the component (A), from the viewpoint of preventing loss of the self-selective adhesiveness after drying the hair cosmetic composition, the content of a propyleneoxy group in the total amount of the component (A) is preferably 1% by mass or more, more preferably 3% by mass or more and even more preferably 5% by mass or more. Furthermore, from the viewpoint of obtaining excellent solubility and dispersibility in water and obtaining sufficient self-selective adhesiveness after drying the hair cosmetic composition, the content of the propyleneoxy group in the total amount of component (A) is preferably 50% by mass or less, more preferably 40% by mass or less and even more preferably 30% by mass or less.

From the viewpoint of obtaining sufficient selective self-adhesiveness after drying the hair cosmetic composition, the oxyalkylene polymer as the component (A) has a weight average molecular weight of preferably 5,000 or more, more preferably 7,000 or more and even more preferably 10,000 or more. Furthermore, from the viewpoint of showing sufficient self-selective adhesiveness after drying the hair cosmetic composition and avoiding the increase of viscosity of the composition for ease of use, the weight average molecular weight is preferably 1,500,000 or less, more preferably 600,000 or less and even more preferably 200,000 or less.

A method for preparing the component (A) is not especially limited. The component (A) is preferably prepared through ring opening polymerization of a cyclic compound containing oxygen such as alkyleneoxide, and either a basic catalyst or an acidic catalyst may be used as a catalyst for the polymerization.

The content of the oxyalkylene polymer as the component (A) in the hair cosmetic composition of the present invention (in the case of an aerosol product, the content in a stock solution is meant and hereinafter the same meaning is used for aerosols below) is preferably 0.01% by mass or more, more preferably 0.05% by mass or more and even more preferably 0.1% by mass or more from the viewpoint of obtaining excellent styling performance and hairstyle retention after drying the hair cosmetic composition. Furthermore, from the viewpoint of securing appropriate ease of style, the content is preferably 20% by mass or less, more preferably 15% by mass or less and even more preferably 10% by mass or less.

[(B): Polymer Comprising Component Units (b1) and (b2)]

In the polymer comprising the component units (b1) and (b2), the component unit (b1) is present as an unneutralized acidic type component from the viewpoint of obtaining a hair cosmetic composition excellent in ability to set the hair set and restyling the hair and free from stiffness. The component unit (b1) may be partially neutralized and it is necessary for the hair cosmetic composition to have a pH of 6 or less, preferably 5.9 or less and more preferably 5.8 or less. On the other hand, from the viewpoint of obtaining excellent self-selective adhesiveness after drying the hair cosmetic composition, the hair cosmetic composition preferably has a pH of 2.0 or more, more preferably 2.5 or more, even more preferably 3.0 or more and even more preferably 3.5 or more. Besides, in the polymer as the component (B), an equivalent ratio of a base used for neutralization of a carboxy group present in the unneutralized acid type component is preferably 0 to 40%, more preferably 0 to 20% and even more preferably 0 to 10%.

The substituents $R^1$ and $R^2$ of the component units (b1) and (b2) represent a hydrogen atom or a methyl group. The substituent $R^3$ represents a hydrocarbon group having 2 to 20 carbon atoms, and the hydrocarbon group may be either saturated or unsaturated and either straight or branched. The carbon number of the substituent $R^3$ is preferably 10 or more, and more preferably 14 or more, from the viewpoint of making the hair cosmetic composition less sticky, and is preferably 22 or less, more preferably 20 or less and even more preferably 18 or less, from the viewpoint of obtaining excellent solubility and dispersibility of the component (B) in water or lower alcohol.

Furthermore, mass ratio of the component unit (b1)/(b2) in the component (B) is preferably 50/50 or more, more preferably 55/45 or more and even more preferably 60/40 or more, from the viewpoint of obtaining excellent selective self-adhesiveness after drying the hair cosmetic composition. The mass ratio (b1)/(b2) is 100/0 or less, and is preferably 90/10 or less and more preferably 80/20 or less, from the viewpoint of suppressing hardening of a film formed on hair for obtaining excellent restyling performance.

The representative component units (b1) and (b2) are derived from (meth)acrylic acid and (meth)acrylate, respectively. In addition to these, the structures of the component units (b1) and (b2) may be ultimately formed from compounds other than (meth)acrylic acid and (meth)acrylate in the structure of the component (B). For example, the component units (b1) and (b2) may be formed through polymerization of methyl vinyl ether and maleic anhydride.

Although the polymer as the component (B) may contain a component unit other than the component units (b1) and (b2), the content amount of such a component unit in the total amount of component (B) is preferably 30% by mass or less, more preferably 20% by mass or less and even more preferably 15% by mass or less. Examples of the component unit other than the component units (b1) and (b2) include, for example: nonionic component units which are derived from compounds having a vinyl structure such as vinyl pyrrolidone, vinyl caprolactam and vinyl acetate, and are derived from compounds having structures of alkylacrylamide, N,N-dialkylacrylamide, hydroxyalkyl (meth)acrylate, methoxy PEG (meth)acrylate; cationic component units derived from compounds such as N,N-dimethylaminopropyl acrylamide and dimethylaminoethyl acrylamide; anionic component units derived from monocarboxylic acids other than (meth)acrylic acid such as crotonic acid, dicarboxylic acids such as itaconic acid, maleic acid and fumaric acid, sulfonic acids such as vinyl sulfonic acid, and phosphoric acids such as acryloyloxyethyl phosphate; and amphoteric component units derived from compounds having structures of carboxybetaine, sulfobetaine, phosphobetaine.

A method for preparing this polymer is not especially limited, and the polymer may be prepared by polymerizing a vinyl monomer capable of forming the component units by polymerization, such as radical polymerization, living polymerization, living radical polymerization, group-transfer polymerization and ring opening polymerization. The type of structure of the polymer employed in this case is not especially limited and may be any one of a random polymer, a block polymer and a graft polymer, and is preferably a random polymer, from the viewpoint of showing sufficient selective self-adhesiveness in combination with the oxyethylene polymer.

The component (B) has a weight average molecular weight of preferably 5,000 or more, more preferably 7,000 or more and even more preferably 10,000 or more, from the viewpoint of obtaining excellent selective self-adhesiveness after drying the hair cosmetic composition. Besides, the weight average molecular weight is preferably 1,000,000 or less, more preferably 100,000 or less and even more preferably 50,000 or less, from the viewpoint of preventing hardening of a film formed on hair for obtaining excellent restyling performance.

A content of the component (B) in the hair cosmetic composition of the present invention is preferably 0.01% by mass or more, more preferably 0.05% by mass or more and even more preferably 0.1% by mass or more, from the viewpoint of obtaining excellent styling performance and hairstyle retention after drying the hair cosmetic composition. Besides, from the viewpoint of obtaining appropriate styling easiness, the content is preferably 20% by mass or less, more preferably 15% by mass or less and even more preferably 10% by mass or less.

A mass ratio between the components (A) and (B) ((A)/(B)) in the hair cosmetic composition of the present invention is preferably 30/70 or more, more preferably 35/65 or more and even more preferably 40/60 or more, from the viewpoint of obtaining excellent selective self-adhesiveness after drying the hair cosmetic composition. Besides, from the viewpoint of obtaining excellent selective self-adhesiveness after drying the hair cosmetic composition, the mass ratio is preferably 70/30 or less, more preferably 65/35 or less and even more preferably 60/40 or less.

[Other Set Polymer]

When another set polymer is contained as an optional component in addition to the components (A) and (B) in the hair cosmetic composition of the present invention, the set retention may be further improved. Examples of such a set polymer include an alkylacrylamide/acrylate/alkylaminoalkylacrylamide/polyethylene glycol methacrylate copolymer described in JP-A-2-180911; an alkylacrylamide/alkylaminoalkylacrylamide/polyethylene glycol methacrylate copolymer described in JP-A-8-291206; (methacryloyloxyethyl carboxybetaine/alkyl methacrylate) copolymers such as YUKAFORMER R205 and YUKAFORMER 301 (both manufactured by Mitsubishi Chemical Corporation) and RAM resin (manufactured by Osaka Organic Chemical Industry Ltd.); (acrylate/lauryl acrylate/stearyl acrylate/ethylamine oxide methacrylate) copolymers such as DIAFORMER Z-651 (manufactured by Mitsubishi Chemical Corporation); acrylic acid/acrylic acid amide/ethyl acrylate copolymers such as Ultrahold 8 and Ultrahold Strong (both manufactured by BASF Japan Ltd.); alkyl acrylate/methacrylic acid/silicone copolymers such as Luviflex Silk (manufactured by BASF Japan Ltd.); polyurethane such as Luviset P.U.R (manufactured by BASF Japan Ltd.); polyvinyl caprolactam such as Luviskol Plus (manufactured by BASF Japan Ltd.); alkyl acrylate copolymers such as Luvimer 100P and Luvimer 30E (both manufactured by BASF Japan Ltd.); (octylacrylamide/hydroxypropyl acrylate/butylaminoethyl methacrylate) copolymers such as Unfoamer 28-4910 and Unfoamer LV-71 (both manufactured by Akzo Nobel); (alkyl acrylate/octylacrylamide) copolymers such as Unfoamer HC (manufactured by Akzo Nobel); (vinyl acetate/crotonic acid/vinyl neodecanoate) copolymers such as Resin 28-2930 (manufactured by Akzo Nobel); polyurethane 14/AMP-acrylate copolymers such as Dynam X (manufactured by Akzo Nobel); diethyl sulfate quaternized (vinyl pyrrolidone/dimethylaminoethyl methacrylate) copolymers (polyquaternium-11) such as Gafquat 734 (manufactured by ISP Japan Ltd.); quaternary ammonium salts of (vinyl pyrrolidone/dimethylaminopropyl methacrylamide) copolymers (polyquaternium-28) such as Conditioneze NT-20 (manufactured by ISP Japan Ltd.); (PVP/vinyl caprolactam/DMAPA acrylate) copolymers such as Aquaflex SF-40 (manufactured ISP Japan Ltd.); (isobutylene/ethyl maleimide/hydroxyethyl maleimide) copolymers such as Aquaflex FX-64 (manufactured by ISP Japan Ltd.); (vinyl pyrrolidone/dimethylaminopropyl methacrylamide/methacryloylaminopropyl lauryl dimethyl ammonium chloride) copolymers (polyquaternium-55) such as Styleze W-20 (manufactured by ISP Japan Ltd.); (vinyl pyrrolidone/DMAPA acrylate) copolymers such as Styleze CC-10 (manufactured by ISP Japan Ltd.); and (vinyl pyrrolidone/vinyl acetate) copolymers such as PVP/VA E-735 (manufactured by ISP Japan Ltd.) and Luviskol VA64P (manufactured by BASF Japan Ltd.).

Among the aforementioned set polymers, the alkylacrylamide/acrylate/alkylaminoalkylacrylamide/polyethylene glycol methacrylate copolymers, the alkylacrylamide/alkylaminoalkylacrylamide/polyethylene glycol methacrylate copolymers, the (methacryloyloxyethyl carboxybetaine/alkyl methacrylate) copolymers, the (octylacrylamide/hydroxypropyl acrylate/butylaminoethyl methacrylate) copolymers, the acrylic acid/acrylic acid amide/ethyl acrylate copolymers, the polyvinyl caprolactam and the (alkyl acrylate/octylacrylamide) copolymers are preferably used, and alkylacrylamide/acrylate/alkylaminoalkylacrylamide/polyethylene glycol methacrylate copolymers, and the alkylacrylamide/alkylaminoalkylacrylamide/polyethylene glycol methacrylate copolymers are more preferably used. Two or more of such set polymers other than the components (A) and (B) may be used in combination.

From the viewpoint of maintaining excellent selective self-adhesiveness of the hair cosmetic composition of the present invention, a mass ratio between the total amount of the components (A) and (B) and the amount of another set polymer ([(A)+(B)]/[another set polymer]) may be preferably 60/40 or more, more preferably 70/30 or more and even more preferably 80/20 or more.

[Medium]

As a solvent (suspension medium), for example, water, lower alcohols (such as ethanol and isopropanol), lactones and the like may be used, and these solvents may be used alone or in combination. From the viewpoint of versatility, solubility and dispersibility of a cosmetic composition, water, ethanol or a mixed system of water and ethanol is preferably used.

[Optional Components]

In addition to the aforementioned components, a plasticizer component can be contained in the hair cosmetic composition of the present invention for the purpose of providing appropriate adhesiveness and re-adhesiveness without loss of the selective self-adhesiveness. Examples of such a plasticizer component include polyols such as glycerin, 1,3-butanediol and dipropylene glycol, and nonionic surfactants.

Furthermore, a cosmetic oil component may be added within a limit of not preventing the effects of the present invention (preferably from 0.1 to 10% by mass). Examples of the cosmetic oil component include glycerides such as castor oil, cacao oil, mink oil, avocado oil and olive oil; waxes such as bees wax, spermaceti wax, lanolin and carnauba wax; higher alcohols such as cetyl alcohol, oleyl alcohol, hexadecyl alcohol, lauryl alcohol, stearyl alcohol, isostearyl alcohol and 2-octyldodecanol; esters such as isopropyl myristate, hexyl laurate, cetyl lactate, propylene glycol monostearate, oleyl oleate, hexadecyl 2-ethylhexanoate and octyldodecyl myristate; hydrocarbon oils such as liquid paraffin, vaseline, squalene and hydrogenated polyisobutene; and silicone derivatives such as dimethylpolysiloxane, methylphenylpolysiloxane, polyether-modified silicone oil, epoxy-modified silicone oil, amino-modified silicone oil and alkyl-modified silicone oil. Furthermore, an emulsifier may be added for stabilizing the cosmetic oil component by emulsification. As the emulsifier, any of anionic, amphoteric, cationic and nonionic surfactants can be used.

Moreover, the hair cosmetic composition of the present invention may contain a perfume or a dye for increasing its consumer value, and an antiseptic agent or an antioxidant for preventing quality deterioration over time of the hair cosmetic composition. Besides, the hair cosmetic composition may contain, for example, a moisture controlling agent such as glycerin or propylene glycol, a curing agent, an antistatic agent, an antifoamer, a dispersant, a thickening agent, an ultraviolet absorber, a coloring dye, a dye fixative, or a propellant, if necessary.

[Dosage Form]

The dosage form of the hair cosmetic composition of the present invention is not especially limited, and the hair cosmetic composition may be in the form of, for example, a transparent liquid, a lotion, an emulsion, a spray (aerosol or non-aerosol) or a foam (aerosol or non-aerosol).

An aerosol hair cosmetic composition is produced by filling the aforementioned hair cosmetic composition together with a propellant in a pressure-resistant container. Examples of the propellant include liquefied petroleum gas (LPG), dimethyl ether (DME), a carbon dioxide gas, a nitrogen gas, and a mixture of these. Alternatively, an alternative Freon such as HFC-152a may be used. From the viewpoint of obtaining excellent spraying performance and excellent adhesion characteristics, the amount of the propellant is, in terms of a mass ratio between a stock solution and the propellant, i.e., a stock solution/propellant ratio, of 5/95 to 99/1 and more preferably 20/80 to 95/5. For obtaining excellent spraying performance and excellent adhesion characteristics, the pressure within the pressure-resistant container is preferably adjusted to 0.12 to 0.45 MPa at a temperature of 25° C.

[Hair Styling Method]

The hair cosmetic composition of the present invention may be suitably used as a hair styling preparation. As a method for using it as a hair styling preparation, namely, a hair styling method, any method may be employed as long as the hair cosmetic composition of the present invention is applied to hair for setting a hairstyle. The hair cosmetic composition of the present invention may be applied to wet hair or to dry hair.

For example, after towel-drying wetted hair, the hair cosmetic composition of the present invention is applied to the hair, and the hair may be dried or set by using a hair iron or a hair dryer. In this manner, the hair may be effectively styled, and the hairstyle may be maintained. Furthermore, after towel-drying the wetted hair, the hair cosmetic composition of the present invention is preferably uniformly applied to the whole hair from the hair roots or the part of the hair on the head generally facing inward toward the skin before drying the hair with a hair dryer, in order to increase the hair volume in appearance and feel.

Alternatively, the hair cosmetic composition of the present invention may be partially applied to a desired part of the dry hair (hair tress) for styling, and may make the desired hair style.

Moreover, after setting a hairstyle with the hair cosmetic composition of the present invention applied to the hair, the set hairstyle may be changed or restyled after the hairstyle is disheveled, without using a hair dryer or a hair iron. Hair restyling after setting the hairstyle once, as above, can be easily performed using fingers.

Preferable embodiments of the hair cosmetic composition described above are shown below.

<1>

A hair cosmetic composition comprising the following components (A) and (B) and having a pH of 6 or less:

(A) an oxyalkylene polymer represented by the following general formula (a1):

-(AO)$_n$— (a1)

wherein A represents an alkylene group having 2 to 6 carbon atoms and n represents a number from 50 to 30,000, provided that n number of AOs consist of at least two alkyleneoxy groups and are arranged through either random polymerization or block polymerization; and (B) a polymer containing a component unit represented by the following general formula (b1) and a component unit represented by the following general formula (b2) in a mass ratio (b1)/(b2) of 50/50 to 100/0:

—(CH$_2$CR$^1$COOH)— (b1)

—(CH$_2$CR$^2$COOR$^3$)— (b2)

wherein R$^1$ and R$^2$ represent a hydrogen atom or a methyl group and R$^3$ represents a hydrocarbon group having 2 to 20 carbon atoms.

<2>

The hair cosmetic composition according to <1>, wherein the oxyalkylene polymer as the component (A) has a weight average molecular weight of preferably 5,000 to 1,500,000, more preferably 7,000 to 600,000 and even preferably 10,000 to 200,000.

<3>

The hair cosmetic composition according to <1> or <2>, wherein (AO)$_n$ of the oxyalkylene polymer as the component (A) has a random structure.

<4>

The hair cosmetic composition according to any one of <1> to <3>, wherein n number of AOs of the component (A) is preferably a combination of two or more alkyleneoxy groups each having 2 to 4 carbon atoms and more preferably a combination of an ethyleneoxy group and a propyleneoxy group.

<5>

The hair cosmetic composition according to any one of <1> to <4>, wherein a content of a propyleneoxy group in the total amount of the component (A) is preferably 1 to 50% by mass, more preferably 3 to 40% by mass and even more preferably 5 to 30% by mass.

<6>

The hair cosmetic composition according to any one of <1> to <5>, wherein the polymer as the component (B) has a weight average molecular weight of preferably 5,000 to 1,000,000, more preferably 7,000 to 100,000 and even more preferably 10,000 to 50,000.

<7>

The hair cosmetic composition according to any one of <1> to <6>, wherein a content of the component (A) is preferably 0.01 to 20% by mass, more preferably 0.05 to 15% by mass and even more preferably 0.1 to 10% by mass.

<8>

The hair cosmetic composition according to any one of <1> to <7>, wherein a content of the component (B) is preferably 0.01 to 20% by mass, more preferably 0.05 to 15% by mass and even more preferably 0.1 to 10% by mass.

<9>

The hair cosmetic composition according to any one of <1> to <8>, wherein a medium used therein is preferably water, lower alcohol or a lactone, more preferably water, ethanol or a mixed system of water and ethanol, and even more preferably water.

<10>

The hair cosmetic composition according to any one of <1> to <9>, wherein the component (A) has a degree of polymerization of preferably 100 or more and more preferably 150 or more, and preferably 12,000 or less and more preferably 4,000 or less.

<11>

The hair cosmetic composition according to any one of <1> to <10>, wherein the hair cosmetic composition has a pH of preferably 5.9 or less and more preferably 5.8 or less, and preferably 2.0 or more, more preferably 2.5 or more, still more preferably 3.0 or more and much more preferably 3.5 or more.

<12>

The hair cosmetic composition according to any one of <1> to <11>, wherein R$^3$ of the component (B) has a carbon number of preferably 10 or more and more preferably 14 or more, and preferably 22 or less, more preferably 20 or less and even more preferably 18 or less.

<13>

The hair cosmetic composition according to any one of <1> to <12>, wherein the mass ratio between the component units (b1) and (b2) ((b1)/(b2)) in the component (B) is preferably 55/45 or more and more preferably 60/40 or more, and preferably 90/10 or less and more preferably 80/20 or less.

<14>

The hair cosmetic composition according to any one of <1> to <13>, wherein a mass ratio between the component (A) and the component (B) ((A)/(B)) is preferably 30/70 or more, more preferably 35/65 or more and even more preferably 40/60 or more, and preferably 70/30 or less, more preferably 65/35 or less and even more preferably 60/40 or less.

<15>

A method for hair styling, comprising applying a hair cosmetic composition according to any one of <1> to <14> to hair, and setting a hairstyle.

<16>

A use of a hair cosmetic composition according to any one of <1> to <14> as a hair styling preparation.

The following examples further describe and demonstrate embodiments of the present invention. The examples are given solely for the purpose of illustration and are not to be construed as limitations of the present invention.

EXAMPLES

In the examples described below, the weight average molecular weight of each polymer was measured by the method described above.

Examples 1 to 22 and Comparative Examples 1 to 11

Pump mist compositions respectively having formulations shown in Tables 1 to 4 were prepared by a general method. The pH of each composition was adjusted by a general method by using 2-amino-2-methyl-1-propanol in Examples 1 to 20 and Comparative Examples 1 to 11 and by using sodium hydroxide in Example 21. In Example 22, the pH was adjusted by adding lactic acid to the formulation of Example 19. These pump mist compositions were evaluated by the following evaluation methods.

<Sensory Evaluation Method for Self-Adhesive Force/Other-Adhesive Force>

A dry composition was prepared by applying 0.4 g of each pump mist composition onto a region of 30 mm×20 mm on a resin sheet of a biaxial oriented PET film (manufactured by Toray Industries, Inc.; Lumirror L-38-T60) and allowing the resulting sheet to stand at 25° C. and 40% RH for 24 hours. The thus prepared dry composition was sensorially evaluated for self-adhesive force and other-adhesive force under an environment of 25° C. and 40 to 65% RH as follows.

(Self-Adhesive Force)

Two dry cast films are adhered to each other with a force of 1 g/cm$^2$, and a resisting force arising in peeling it at a peeling rate of 30 mm/sec in T-shape peeling mode 1 second after the adhesion was evaluated by an expert panelist to be scored in 5 grades, on the assumption that the self-adhesive force in Example 1 shall be scored as 5 and that in Comparative Example 4 shall be scored as 1.

(Other-Adhesive Force)

Each dry cast film was pressed down with a finger with a force of 1 g/cm$^2$, and a resisting force arising in taking the finger off at 100 mm/s 0.1 second after pressing was evaluated by an expert panelist to be scored in 5 grades, on the assumption that the other-adhesive force in Comparative Example 8 shall be scored as 5 and that in Example 1 shall be scored as 1.

<Evaluation of Styling Performance>

A tress with a length of 25 cm and a weight of 3 g was wetted with water and then dried with a towel. Thereafter, the tress was spirally wound around a rod having a diameter of 22 mm and then allowed to stand at 25° C. and 65% RH for 24 hours, and thereafter, the rod was taken off the tress, so as to obtain a spirally styled tress. Subsequently, the hair cosmetic composition of each of the formulations was applied by 1 g to the tress by means of a pump mist, and then the tress was unwound using the hands and styled into another type of a curly hairstyle. An expert panelist evaluated the hair styling performance shown at this point in accordance with the following criteria, from the viewpoint of whether or not the hair flow was evenly arranged and the hair could be curled as desired without fly away hair.

a: Strong hair styling ability
    b: Slightly strong hair styling ability
    c: Slightly weak hair styling ability
    d: Weak or no hair styling ability <Evaluation of Stickiness to Fingers>

Feel of an evaluation sample prepared by a method similar to that described above was evaluated by an expert panelist in accordance with the following criteria:

a: No stickiness
    b: Substantially no stickiness
    c: Slight stickiness
    d: Has Stickiness <Evaluation of Stiffness>

Feel of an evaluation sample prepared by a method similar to that described above was evaluated by an expert panelist in accordance with the following criteria:

a: No stiffness
    b: Substantially no stiffness
    c: Slight stiffness
    d: Stiff <Evaluation of Restyling Performance>

An evaluation sample prepared by a method similar to that described above was combed five times (with Delrin Smooth Comb #802 (straight); Takigawa Co., Ltd.) so as to disheveled the set style of the tress, and thereafter, an operation to restore the tress into the original style with fingers was performed. An expert panelist evaluated the hair restyling performance shown at this point in accordance with the following criteria, from the viewpoint of whether or not the tress was restored into the original style without losing curls and not having fly away hair:

a: Strong ability to restyling
    b: Slightly strong restyling ability
    c: Slightly weak restyling ability
    d: Weak or no restyling ability <Evaluation of Stability of Composition>

Each of the compositions shown in Tables 1 to 4 was charged in a glass container and stored at 50° C. for 1 month under a shade where substantially no light penetrates through. Thereafter, the sample was subjected to the sensory evaluation for the self-adhesive force and the other-adhesive force performed in the aforementioned manner, so as to evaluate degradation of performance in accordance with the following criteria. A sample giving a poor result in the sensory evaluation for the self-adhesive force and the other-adhesive force before storage was not evaluated for stability.

a: Equivalent to that attained before storage
    b: Selective self-adhesiveness degraded as compared with that attained before storage (specifically, the self-adhesive force lowered, or the other-adhesive force increased, or both)

Notes (*1 to *14) given in Tables 1 to 4 are as follows:

*1 Weight average molecular weight: 5000, EO/PO mass ratio=70/30 (ADEKA Corporation, Adeka polyether PR5007)

(degree of polymerization calculated based on EO/PO mass ratio: EO=80, PO=26)

*2 Weight average molecular weight: 100000, EO/PO mass ratio=90/10

(degree of polymerization calculated based on EO/PO mass ratio: EO=2045, PO=172)

*3 Weight average molecular weight: 100000, EO/PO mass ratio=80/20
(degree of polymerization calculated based on EO/PO mass ratio: EO=1818, PO=345)

*4 Weight average molecular weight: 100000, EO/PO mass ratio=60/40
(degree of polymerization calculated based on EO/PO mass ratio: EO=1364, PO=690)

*5 $R^3=C_{18}$ alkyl, (b1)/(b2)=67/33 (mass ratio), weight average molecular weight: 100000, $R^1$ and $R^2$=H

*6 $R^3=C_{18}$ alkyl, (b1)/(b2)=67/33 (mass ratio), weight average molecular weight: 20000, $R^1$ and $R^2$=H

*7 $R^3=C_{18}$ alkyl, (b1)/(b2)=67/33 (mass ratio), weight average molecular weight: 50000, $R^1$ and $R^2$=H

*8 $R^3=C_{14}$ alkyl, (b1)/(b2)=67/33 (mass ratio), weight average molecular weight: 20000, $R^1$ and $R^2$=H

*9 $R^3=C_{18}$ alkyl, (b1)/(b2)=80/20 (mass ratio), weight average molecular weight: 20000, $R^1$ and $R^2$=H

*10 $R^3=C_{18}$ alkyl, (b1)/(b2)=80/20 (mass ratio), weight average molecular weight: 20000, $R^1$ and $R^2$=$CH_3$

*11 (b1)/(b2)=100/0 (mass ratio), weight average molecular weight: 5000, $R^1$=$CH_3$

*12 YUKAFORMER 301 (manufactured by Mitsubishi Chemical Corporation (in terms of dry solid contents))

*13 Polymer 2 obtained in Synthesis Example 2 of Patent Document 4 (JP-A-2010-168293)

*14 No stickiness inevitably because of poor ability to restyling hair due to too hard film (*1 to *4 and *13 contain 100 ppm of dihydroxy toluene in solid contents)

TABLE 1

| % by mass | | | Example 1 | 2 | 3 | 4 | 5 | 6 | 7 | 8 |
|---|---|---|---|---|---|---|---|---|---|---|
| (A) | Oxyalkylene polymer (*1) | | — | 1.5 | — | — | — | — | — | — |
| | Oxyalkylene polymer (*2) | | 1.5 | — | — | — | 1.5 | 1.5 | 1.5 | 1.5 |
| | Oxyalkylene polymer (*3) | | — | — | 1.5 | — | — | — | — | — |
| | Oxyalkylene polymer (*4) | | — | — | — | 1.5 | — | — | — | — |
| (B) | Alkyl acrylate/acrylic acid copolymer (*5) | | — | — | — | — | 1.5 | — | — | — |
| | Alkyl acrylate/acrylic acid copolymer (*6) | | 1.5 | 1.5 | 1.5 | 1.5 | — | — | — | — |
| | Alkyl acrylate/acrylic acid copolymer (*7) | | — | — | — | — | — | 1.5 | — | — |
| | Alkyl acrylate/acrylic acid copolymer (*8) | | — | — | — | — | — | — | 1.5 | — |
| | Alkyl acrylate/acrylic acid copolymer (*9) | | — | — | — | — | — | — | — | 1.5 |
| Other components | 1,3-Butanediol | | — | — | — | — | — | — | — | — |
| | Polyethylene glycol (weight average molecular weight: 400) | | — | — | — | — | — | — | — | — |
| | Ion-exchanged water | | balance | balance | balance | balance | balance | balance | balance | balance |
| pH of formulation | | | 4.5 | 4.5 | 4.5 | 4.5 | 4.5 | 4.5 | 4.5 | 4.5 |
| Compounding ratio (A)/(B) | | | 50/50 | 50/50 | 50/50 | 50/50 | 50/50 | 50/50 | 50/50 | 50/50 |
| Self-adhesive force (sensory score) | | | 5 | 3 | 4 | 4 | 3 | 4 | 4 | 4 |
| Other-adhesive force (sensory score) | | | 1 | 2 | 2 | 2 | 1 | 2 | 2 | 2 |
| Styling performance | | | a | b | a | a | b | a | a | a |
| Restyling performance | | | a | a | b | b | b | b | b | b |
| Stickiness evaluation | | | a | b | a | a | a | a | a | a |
| Stiffness evaluation | | | a | b | a | a | b | a | a | a |
| Storage stability | | | a | a | a | a | a | a | a | a |

TABLE 2

| % by mass | | Example 9 | 10 | 11 | 12 | 13 | 14 | 15 | 16 | 17 | 18 |
|---|---|---|---|---|---|---|---|---|---|---|---|
| (A) | Oxyalkylene polymer (*1) | — | — | — | — | — | — | — | — | — | — |
| | Oxyalkylene polymer (*2) | 2.1 | 1.8 | 1.2 | 0.9 | 1.5 | 1.5 | 1.5 | 1.5 | 1.5 | 1.5 |
| | Oxyalkylene polymer (*3) | — | — | — | — | — | — | — | — | — | — |
| | Oxyalkylene polymer (*4) | — | — | — | — | — | — | — | — | — | — |
| (B) | Alkyl acrylate/acrylic acid copolymer (*5) | — | — | — | — | — | — | — | — | — | — |
| | Alkyl acrylate/acrylic acid copolymer (*6) | 0.9 | 1.2 | 1.8 | 2.1 | 1.5 | 1.5 | 1.5 | 1.5 | — | 1.5 |
| | Alkyl acrylate/acrylic acid copolymer (*7) | — | — | — | — | — | — | — | — | — | — |
| | Alkyl acrylate/acrylic acid copolymer (*8) | — | — | — | — | — | — | — | — | — | — |
| | Alkyl acrylate/acrylic acid copolymer (*9) | — | — | — | — | — | — | — | — | — | — |
| | Alkyl methacrylate/methacrylic acid copolymer (*10) | — | — | — | — | — | — | — | — | 1.5 | — |
| Other components | 1,3-Butanediol | — | — | — | — | 0.1 | — | — | — | — | — |
| | Polyethylene glycol (weight average molecular weight: 400) | — | — | — | — | — | 0.1 | — | — | — | — |
| | Ethanol | — | — | — | — | — | — | — | — | 20 | 50 |
| | Ion-exchanged water | balance | balance | balance | balance | balance | balance | balance | balance | balance | balance |
| pH of formulation | | 4.5 | 4.5 | 4.5 | 4.5 | 4.5 | 4.5 | 5 | 6 | 4.5 | 5.6 |
| Mass ratio (A)/(B) | | 70/30 | 60/40 | 40/60 | 30/70 | 50/50 | 50/50 | 50/50 | 50/50 | 50/50 | 50/50 |
| Self-adhesive force (sensory score) | | 3 | 4 | 4 | 3 | 4 | 3 | 4 | 3 | 3 | 4 |

TABLE 2-continued

| % by mass | Example | | | | | | | | | |
|---|---|---|---|---|---|---|---|---|---|---|
| | 9 | 10 | 11 | 12 | 13 | 14 | 15 | 16 | 17 | 18 |
| Other-adhesive force (sensory score) | 1 | 2 | 2 | 1 | 2 | 1 | 1 | 1 | 1 | 1 |
| Styling performance | b | a | a | b | a | b | a | b | b | a |
| Restyling performance | b | b | b | b | b | b | b | b | b | b |
| Stickiness evaluation | a | a | a | a | a | a | a | a | a | a |
| Stiffness evaluation | b | a | a | b | a | b | a | b | b | a |
| Storage stability | a | a | a | a | a | a | a | a | a | a |

TABLE 3

| | % by mass | Example | | | |
|---|---|---|---|---|---|
| | | 19 | 20 | 21 | 22 |
| (A) | Oxyalkylene polymer (*2) | 1.5 | 1.56 | 1.5 | 1.5 |
| (B) | Alkyl acrylate/acrylic acid copolymer (*6) | 1.5 | — | 1.5 | 1.5 |
| | Poly(methacrylic acid) (*11) | — | 0.84 | — | — |
| Other components | Polyethylene glycol (weight average molecular weight: 400) | — | 1.2 | — | — |
| | Ion-exchanged water | balance | balance | balance | balance |
| pH of formulation | | 3.89 | 3.63 | 4.58 | 3.38 |
| Compounding ratio (A)/(B) | | 50/50 | 65/35 | 50/50 | 50/50 |
| Self-adhesive force (sensory score) | | 5 | 3 | 4 | 4 |
| Other-adhesive force (sensory score) | | 1 | 1 | 1 | 1 |
| Styling performance | | a | b | a | a |
| Restyling performance | | a | b | b | a |
| Stickiness evaluation | | a | a | a | b |
| Stiffness evaluation | | a | a | b | a |
| Storage stability | | a | a | a | a |

TABLE 4

| | | % by mass | Comparative Example | | | | | | | | | | |
|---|---|---|---|---|---|---|---|---|---|---|---|---|---|
| | | | 1 | 2 | 3 | 4 | 5 | 6 | 7 | 8 | 9 | 10 | 11 |
| (A) | | Oxyalkylene polymer (*1) | — | 3 | — | — | — | — | — | — | — | — | — |
| | | Oxyalkylene polymer (*2) | — | — | 3 | — | — | — | — | — | 1.5 | — | — |
| (B) | | Alkyl acrylate/acrylic acid copolymer (*5) | — | — | — | 3 | — | 1.5 | 1.5 | 1.5 | 1.5 | — | — |
| | | Alkyl acrylate/acrylic acid copolymer (*6) | — | — | — | — | 3 | — | — | — | — | — | 1.5 |
| Other components | (A') | Polyethylene glycol (weight average molecular weight: 400) | 1.5 | — | — | — | — | 1.5 | — | — | — | 5 | — |
| | | Polyethylene glycol (weight average molecular weight: 1540) | 1.5 | — | — | — | — | — | — | — | — | — | — |
| | | Polyethylene glycol (weight average molecular weight: 6000) | — | — | — | — | — | — | — | 1.5 | — | — | — |
| | | Polyethylene glycol (weight average molecular weight: 20000) | — | — | — | — | — | — | — | — | — | 5 | — |
| | | Polyethylene glycol (weight average molecular weight: 100000) | — | — | — | — | — | — | — | — | — | — | — |
| | (B') | Methacryloyloxyethyl carboxybetaine/alkyl methacrylate copolymer (*12) | — | — | — | — | — | — | — | — | — | 2 | — |
| | | Sorbitol | — | — | — | — | — | — | — | — | — | 5 | — |
| | | Polyether polycarbonate (*13) | — | — | — | — | — | — | — | — | — | — | 1.5 |
| | | Ethanol | — | — | — | — | — | — | — | — | — | 40 | — |
| | | Ion-exchanged water | balance | balance | balance | balance | balance | balance | balance | balance | balance | balance | balance |
| pH of formulation | | | 7 | 7 | 7 | 4.5 | 4.5 | 4.5 | 4.5 | 4.5 | 6.5 | 7 | 4.5 |
| Mass ratio (A)/(B), (A')/(B) or (A')/(B') | | | 100/0 | 100/0 | 100/0 | 0/100 | 0/100 | 50/50 | 50/50 | 50/50 | 50/50 | 71/29 | — |
| Self-adhesive force (sensory score) | | | 2 | 2 | 1 | 1 | 1 | 5 | 5 | 5 | 2 | 3 | 5 |
| Other-adhesive force (sensory score) | | | 4 | 3 | 1 | 1 | 1 | 5 | 5 | 5 | 1 | 5 | 2 |

TABLE 4-continued

| % by mass | Comparative Example | | | | | | | | | | |
|---|---|---|---|---|---|---|---|---|---|---|---|
| | 1 | 2 | 3 | 4 | 5 | 6 | 7 | 8 | 9 | 10 | 11 |
| Styling performance | c | c | d | c | c | c | c | c | c | c | a |
| Restyling performance | c | c | d | d | d | c | d | d | d | c | b |
| Stickiness evaluation | d | d | b*14 | b*14 | b*14 | d | d | d | b*14 | d | b |
| Stiffness evaluation | c | c | c | d | d | d | d | d | c | c | b |
| Storage stability | — | — | — | — | — | — | — | — | — | — | b |

Formulation Example 1

Non-Aerosol Hair Foam Product (pH=4.5)

| | (% by mass) |
|---|---|
| Oxyalkylene polymer (*2) | 3.0 |
| Alkyl acrylate/acrylic acid copolymer (*6) | 2.5 |
| Sodium lauryl sulfate | 0.3 |
| Perfume | 0.1 |
| 2-Amino-2-methyl-1-propanol | q.s. |
| Water | balance |

[Hair Styling Method]

Hair which has begun to lose a permanent wave is wetted and then dried with a towel. Thereafter, a non-aerosol hair foam product of Formulation Example 1 is applied thereto in an amount sufficient for spreading all over (approximately 0.5 to 6 g), and the hair is dried with a dryer in such a manner as to scrunch up.

Formulation Example 2

Aerosol Hair Foam Product

| | (% by mass) |
|---|---|
| <Stock solution> | |
| Oxyalkylene polymer (*4) | 2.0 |
| Alkyl acrylate/acrylic acid copolymer (*6) | 2.0 |
| Polyethylene glycol (weight average molecular weight: 400) | 0.5 |
| Sodium lauryl sulfate | 0.3 |
| Perfume | 0.1 |
| 2-Amino-2-methyl-1-propanol | q.s. |
| Water | balance |
| pH of stock solution = 4.5 | |
| <Propellant> | |
| LPG (0.44 MPa) | |

Stock solution:propellant = 93:7 (mass ratio)

[Hair Styling Method]

An aerosol hair foam product of Formula Example 2 is applied to half dried hair from hair roots or part of the hair on the head generally facing inward toward the skin thereof in an amount sufficient for spreading all over the hair (approximately 0.5 to 6 g), and then the hair is dried with a dryer while finger combing for obtaining the desired volume and hair flow.

Formulation Example 3

Hair Gel Product (pH=4.5)

| | (% by mass) |
|---|---|
| Oxyalkylene polymer (weight average molecular weight: 1000000, EO/PO mass ratio = 90/10) | 2.0 |
| Alkyl acrylate/acrylic acid copolymer (*8) | 2.0 |
| Dipropylene glycol | 0.1 |
| Perfume | 0.1 |
| 2-Amino-2-methyl-1-propanol | q.s. |
| Water | balance |

[Hair Styling Method]

A hair gel product of Formulation Example 3 is applied to hair ends of dry hair in a proper amount (approximately 0.5 to 2 g), and after lightly pinching and twirling the hair ends so as to form bundles or curly ends, the hair is naturally dried.

Formulation Example 4

Hair Gel Product (pH=4.0)

| | (% by mass) |
|---|---|
| Oxyalkylene polymer (weight average molecular weight: 1000000, EO/PO mass ratio = 80/20) | 2.0 |
| Alkyl acrylate/acrylic acid copolymer (*6) | 1.5 |
| Perfume | 0.1 |
| 2-Amino-2-methyl-1-propanol | q.s. |
| Water | balance |

[Hair Styling Method]

A hair gel product of Formulation Example 4 is uniformly applied to half dried hair from hair roots or part of the hair on the head generally facing inward toward the skin in an amount sufficient for spreading all over (approximately 0.5 to 6 g), and then the hair is dried with a dryer while finger combing for obtaining desired volume and hair flow.

Formulation Example 5

Hair Mist Product (pH=5.0)

| | (% by mass) |
|---|---|
| Oxyalkylene polymer (*2) | 0.5 |
| Alkyl acrylate/acrylic acid copolymer (*6) | 0.5 |
| Polyethylene glycol (weight average molecular weight: 400) | 0.1 |
| Glycerin | 0.1 |

-continued

| | (% by mass) |
|---|---|
| Perfume | 0.1 |
| 2-Amino-2-methyl-1-propanol | q.s. |
| Water | balance |

[Hair Styling Method]

A hair mist of Formulation Example 5 is sprayed to dry straight hair in an amount sufficient for making the whole hair damp (approximately 0.5 to 6 g) and spread thoroughly with the hands, and then, hair styling is performed with a curling iron set to 100 to 200° C.

The invention claimed is:

1. A hair cosmetic composition, comprising:
   (A) an oxyalkylene polymer represented by formula (a1):

$$-(AO)_n- \quad (a1)$$

wherein each A independently represents an alkylene group having 2 to 6 carbon atoms, n represents a number from 50 to 30,000, and at least two different AO groups are present in the oxyalkylene polymer and are arranged randomly or in blocks; and
   (B) a polymer comprising a component unit represented by formula (b1) and a component unit represented by formula (b2) in a mass ratio (b1)/(b2) in a range of from 50/50 to 100/0:

$$-(CH_2CR^1COOH)- \quad (b1)$$

$$-(CH_2CR^2COOR^3)- \quad (b2)$$

wherein each of $R^1$ and $R^2$ independently represents a hydrogen atom or a methyl group, and $R^3$ represents a hydrocarbon group having from 2 to 20 carbon atoms;
   wherein:
   a mass ratio of the oxyalkylene polymer (A) to the polymer (B) ((A)/(B)) is in a range of from 30/70 to 70/30; and
   the composition has a pH of 6 or less.

2. The hair cosmetic composition according to claim 1, wherein the oxyalkylene polymer (A) has a weight average molecular weight of from 5,000 to 1,500,000.

3. The hair cosmetic composition according to claim 1, wherein the at least two different AO groups are arranged randomly in the oxyalkylene polymer (A).

4. The hair cosmetic composition according to claim 1, wherein the oxyalkylene polymer (A) contains a propyleneoxy group in an amount of from 1 to 50% by mass based on a total mass of the oxyalkylene polymer (A).

5. The hair cosmetic composition according to claim 1, wherein the polymer (B) has a weight average molecular weight of from 5,000 to 1,000,000.

6. The hair cosmetic composition according to claim 1, wherein the oxyalkylene polymer (A) is present in an amount of from 0.01 to 20% by mass based on a total mass of the hair cosmetic composition.

7. The hair cosmetic composition according to claim 1, wherein the polymer (B) is present in an amount of from 0.01 to 20% by mass based on a total mass of the hair cosmetic composition.

8. The hair cosmetic composition according to claim 1, comprising a solvent, wherein the solvent comprises at least one of water, a lower alcohol, and a lactone.

9. The hair cosmetic composition according to claim 1, wherein at least two different AO groups of the oxyalkylene polymer (A) contain from 2 to 4 carbon atoms.

10. The hair cosmetic composition according to claim 1, wherein the oxyalkylene polymer (A) has a degree of polymerization in a range of from 100 to 12,000.

11. The hair cosmetic composition according to claim 1, wherein the hair cosmetic composition has a pH in a range of from 2.0 to 5.9.

12. The hair cosmetic composition according to claim 1, wherein the mass ratio of component unit (b1) to component unit (b2) ((b1)/(b2)) in the polymer (B) is in a range of from 55/45 to 90/10.

13. The hair cosmetic composition according to claim 1, wherein $R^3$ of the polymer (B) has a carbon number in a range of from 10 to 22.

14. The hair cosmetic composition according to claim 1, wherein the mass ratio of the oxyalkylene polymer (A) to the polymer (B) ((A)/(B)) is in a range of from 35/65 to 65/35.

15. The hair cosmetic composition according to claim 2, wherein the at least two different AO groups are arranged randomly in the oxyalkylene polymer (A).

16. The hair cosmetic composition according to claim 9, wherein the oxyalkylene polymer (A) contains a propyleneoxy group in an amount of from 1 to 50% by mass based on a total mass of the oxyalkylene polymer (A).

17. The hair cosmetic composition according to claim 16, comprising a solvent, wherein the solvent comprises at least one of water, a lower alcohol, and a lactone.

18. The hair cosmetic composition according to claim 17, wherein the mass ratio of component unit (b1) to component unit (b2) ((b1)/(b2)) in the polymer (B) is in a range of from 55/45 to 90/10.

19. The hair cosmetic composition according to claim 8, wherein the mass ratio of component unit (b1) to component unit (b2) ((b1)/(b2)) in the polymer (B) is in a range of from 55/45 to 90/10.

20. The hair cosmetic composition according to claim 1, wherein the oxyalkylene polymer (A) has a weight average molecular weight of 10,000 or more.

21. The hair cosmetic composition according to claim 1, comprising 2-amino-2-methyl-1-propanol.

* * * * *